US007285775B2

(12) United States Patent
Sievers et al.

(10) Patent No.: US 7,285,775 B2
(45) Date of Patent: Oct. 23, 2007

(54) ENDPOINT DETECTION FOR THE PATTERNING OF LAYERED MATERIALS

(75) Inventors: Michael R. Sievers, Poughkeepsie, NY (US); Siddhartha Panda, Beacon, NY (US); Richard Wise, New Windsor, NY (US)

(73) Assignee: International Business Machines Corporation, Armonk, NY (US)

( * ) Notice: Subject to any disclaimer, the term of this patent is extended or adjusted under 35 U.S.C. 154(b) by 361 days.

(21) Appl. No.: 10/904,883

(22) Filed: Dec. 2, 2004

(65) Prior Publication Data

US 2006/0118718 A1   Jun. 8, 2006

(51) Int. Cl.
*G01N 23/227* (2006.01)
(52) U.S. Cl. .................. 250/305; 250/306; 250/307; 378/89
(58) Field of Classification Search ............... 250/305, 250/306, 307; 378/89, 90, 50, 54
See application file for complete search history.

(56) References Cited

U.S. PATENT DOCUMENTS

| 5,434,422 | A | 7/1995 | Iwamoto et al. |
| 5,635,836 | A | 6/1997 | Kirtley et al. |
| 5,922,179 | A | 7/1999 | Mitro et al. |
| 6,259,092 | B1 | 7/2001 | Brizzolara et al. |
| 6,365,905 | B1 | 4/2002 | Koyama et al. |
| 6,407,850 | B1 | 6/2002 | Rojo et al. |
| 6,782,072 | B2 | 8/2004 | Lin |
| 6,800,852 | B2 * | 10/2004 | Larson et al. ............... 250/305 |
| 6,891,158 | B2 * | 5/2005 | Larson et al. ............... 250/305 |
| 2002/0005492 | A1 | 1/2002 | Hashikawa et al. |
| 2002/0050565 | A1 | 5/2002 | Tokuda et al. |
| 2003/0210759 | A1 * | 11/2003 | Iwamura et al. ............ 376/156 |
| 2004/0060904 | A1 | 4/2004 | Herschbein et al. |
| 2004/0112857 | A1 | 6/2004 | Herschbein et al. |
| 2004/0129879 | A1 | 7/2004 | Furiki et al. |
| 2004/0132287 | A1 | 7/2004 | Fischer et al. |

FOREIGN PATENT DOCUMENTS

| EP | 4031676 A1 | 4/1992 |
| JP | 2000030658 | 1/2000 |

OTHER PUBLICATIONS

Students abstracts: LBNL—Materials Sciences, "Student Abstracts: Materials Sciences at LBNL", http://www.scied.science.doc.gov/scied/Abstracts2003/LBNLms.htm, 2 pages Training Courses 2004, FEI Company, Scanning Electron Microscopy, Small Dualbeam and Applications, 17 pages.
SEM Substages and SPM Accessories from Ernest R. Fallam, Inc., 7 pages, http:www.fallam.com/Sem_subs.htm, "SEM Substages" http://ist-socrates.berkeley.edu/~es196/projects/2000final/mussa.pdf 12 pages http://ist-socrates.berkeley.edu/~es196/projects/2000final/ 2 pages.

* cited by examiner

*Primary Examiner*—Kiet T. Nguyen
(74) *Attorney, Agent, or Firm*—Lisa U. Jaklitsch; Yuanmin Cai

(57) ABSTRACT

Photoelectron emissions are used to detect an endpoint of a thickness alteration of a topmost layer in a set of layers undergoing patterning. The set of layers are irradiated, which causes an emission of photoelectrons. Upon receipt of or absence of a photoelectron emission, patterning endpoint is detected.

19 Claims, 4 Drawing Sheets

OPTICAL EMISSION SPECTROSCOPY

ENDPOINT DETECTION FOR THE PATTERNING OF LAYERED MATERIALS

FIELD OF THE INVENTION

The invention relates generally to the patterning of layered materials, and more particularly to an enhanced method and system for detection of an endpoint to the patterning of such layered materials.

BACKGROUND OF THE INVENTION

Accurate and reproducible patterning, e.g. the removal or deposition of a material, is essential for very large scale integration ("VLSI") devices. Fine line patterning has become increasingly important as devices shrink. Accordingly, endpoint detection is an indispensable tool for the avoidance of undercutting and loss of feature control.

Prior art methods of endpoint detection for the patterning of layered materials include, but are not limited to, interferometry and optical emission spectroscopy. Both interferometry and optical emission spectroscopy determine patterning endpoint.

FIG. 1 illustrates interferometry, a prior art method. With this prior art method, lasers 102 illuminate a layer 110 undergoing patterning and create an interferometric pattern with the returned lasers 104. From the interferometric pattern, the thickness of the layer 110 is measured. Based upon the measured thickness, patterning endpoint is determined.

Interferometry is problematic because as shown in FIG. 1 interferometry is sensitive to topography variations. As shown in FIG. 1, the layer 110 undulates, which causes returned lasers 104 to bounce unpredictably, which in turn creates random interferometric patterns. Random interferometric patterns cannot be used to reliably determine patterning endpoint.

FIG. 2 illustrates optical emission spectroscopy, another prior art method. Optical emission spectroscopy relies upon the principle that plasma generated materials emit light 206. In FIG. 2, the topmost layer 110 is undergoing thickness alteration. Optical emission spectroscopy monitors the patterning of the layered material 220. The layer material can include, but is not limited to, any combination of a semiconductor, dielectric, or conductor. As shown in FIG. 2, as the set of layers 220 undergoes patterning, a material in the topmost layer 110 emits light 206. A photodetector measures the emitted light 206. Based upon the measured emitted light 206, patterning endpoint is determined.

Optical emission spectroscopy is problematic because some materials do not emit light and optical emission spectroscopy cannot discriminate materials by stoichiometry. For example, silicon nitride is used in both stoichiometric and non-stoichiometric form. When either form of silicon nitride is etched, the emitted light that is monitored by optical emission spectroscopy is the same. Therefore, optical emission spectroscopy cannot discriminate between a layer with stoichiometric versus non-stoichiometric silicon nitride.

These and other deficiencies in the prior art are overcome through the invention.

Therefore, there remains a need in the art for an improved method and system for detection of an endpoint for semiconductors.

BRIEF SUMMARY OF THE INVENTION

The invention is directed to a method and system for detection of an endpoint of a thickness alteration of a topmost layer in a set of layers undergoing patterning. An emission of a plurality of photoelectrons from a layer in the set of layers is received. An endpoint of the thickness alteration of the topmost layer is then detected upon either receipt of the emission or absence of the emission.

The invention detects endpoint of a thickness alteration of a layer in a set of layers undergoing patterning. The invention detects endpoint before destruction of the underlying layers. Accordingly, the invention protects the underlying layers, which in turn can improve production. The invention reliably detects endpoint in a manner independent of topography or stoichiometry. Accordingly, the invention improves upon the versatility of patterning endpoint detection, as new materials are used in layered material fabrication.

For at least the foregoing reasons, the invention improves upon endpoint detection for the patterning of layered materials.

BRIEF DESCRIPTION OF THE FIGURES

The features and the element characteristics of the invention are set forth with particularity in the appended claims. The figures are for illustrative purposes only and are not drawn to scale. Furthermore, like numbers represent like features in the drawings. The invention itself, however, both as to organization and method of operation, may best be understood by reference to the detailed description which follows, taken in conjunction with the accompanying figures, in which:

DETAILED DESCRIPTION OF THE PREFERRED EMBODIMENTS

The invention will now be described with reference to the accompanying figures. In the figures, various aspects of the structures have been shown and schematically represented in a simplified manner to more clearly describe and illustrate the invention.

The invention solves the problems associated with prior art endpoint detection methods. In accordance with the invention, a layered material, e.g. a semiconductor, dielectric, or conductor, is irradiated with an x-ray beam, which comprises photons, and a photoelectron emission is caused in response to this irradiation. Photoelectron emissions have signals with energy levels unique to the material of the layer from which the photoelectrons are emitted. The material can be a compound or a element. Because photoelectrons have a short mean free path, photoelectrons generated from materials >9 nm below the surface are not detectable. Such photoelectrons are collisionally de-energized. When the topmost layer becomes thin, however, e.g. $\leq 9.0$ nm, the underlying layer emits a photoelectron emission. Accordingly, endpoint can be detected upon receipt of the photoelectron emission from the underlying layer.

By way of overview and introduction, polysilicon stack etch ("PC etch") will be described in accordance with the method of the invention. At the time of PC etch, a semiconductor wafer has ~2000 A of patterned photoresist, 1000 to 1500 A of underlying polysilicon, and 1000 to 1500 A of further underlying gate oxide. An x-ray beam irradiates the surface of the wafer. A detection system detects a photoelectron signal from the photoresist and polysilicon, but does not detect the photoelectron signal from the gate oxide, which underlies the photoresist and polysilicon. Therefore, the photoelectron signal from the gate oxide is undetectable because of the thickness of the photoresist and polysilicon layers above the gate oxide. As the polysilicon is etched, the thickness of the polysilicon decreases. Once the thickness is ≦9.0 nm, photoelectrons generated from the gate oxide are detectable. Accordingly, at such time a photoelectron emission unique to the gate oxide, such as oxygen, is detectable. A constant photoelectron emission signal of oxygen from the photoresist remains, however that signal becomes a background signal to the photoelectron emission signal of the gate oxide. Accordingly, upon comparison of substantially different signals, patterning endpoint is detected.

Figure 1:
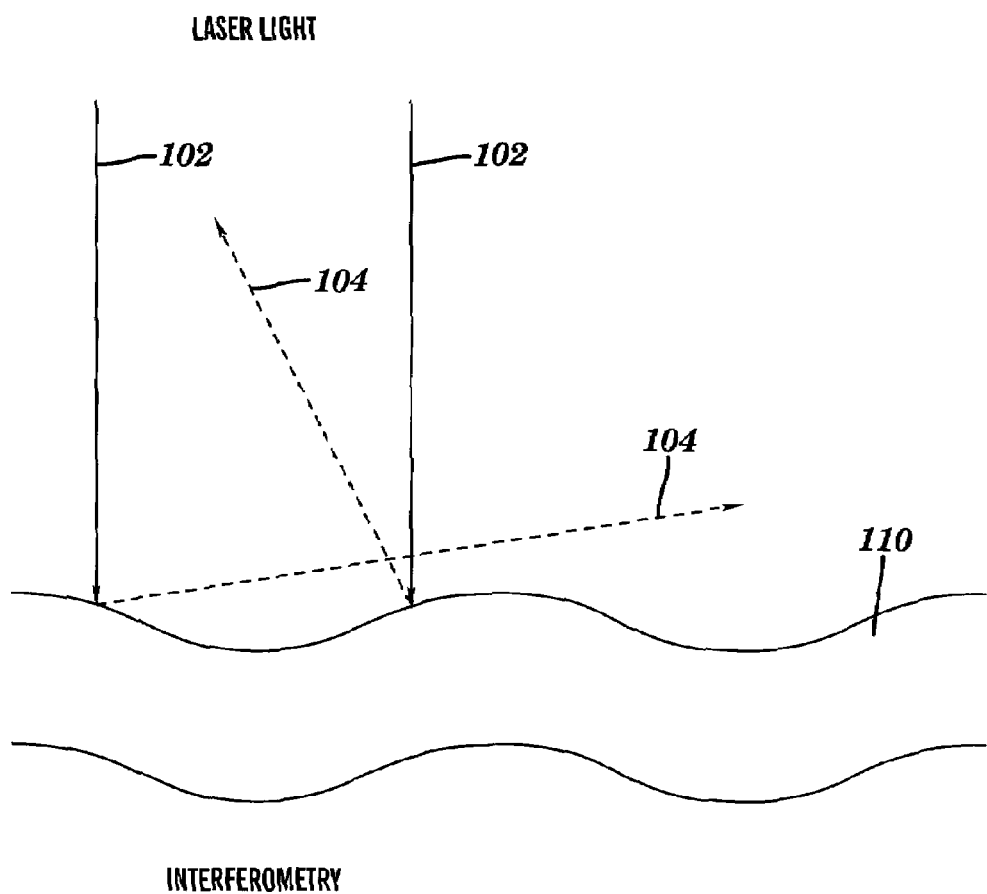
FIG. 1 illustrates an endpoint detection method, according to the prior art.
Figure 2:
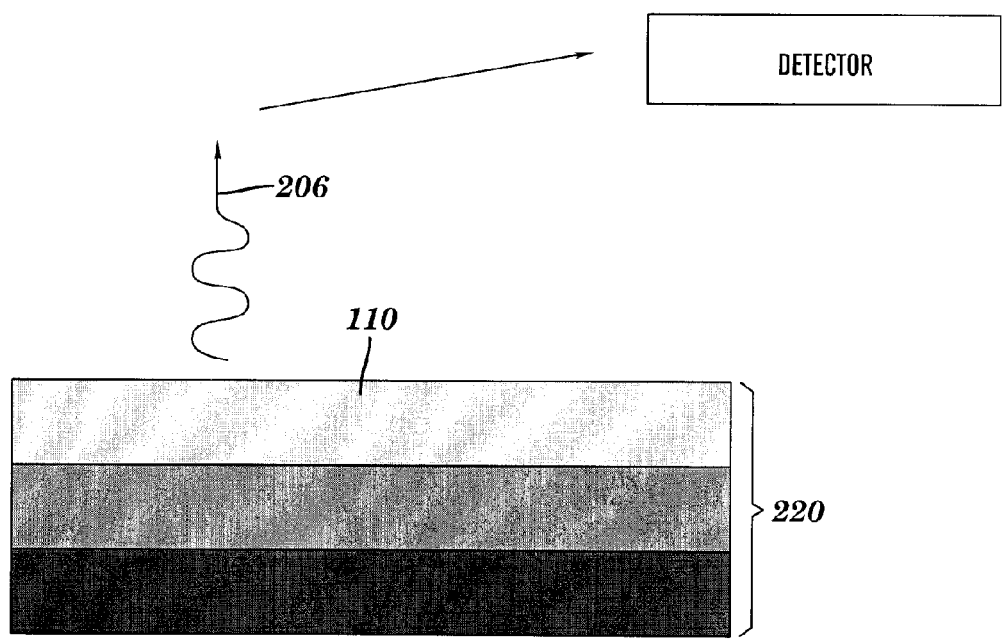
FIG. 2 illustrates an endpoint detection method, according to the prior art.
Figure 3:
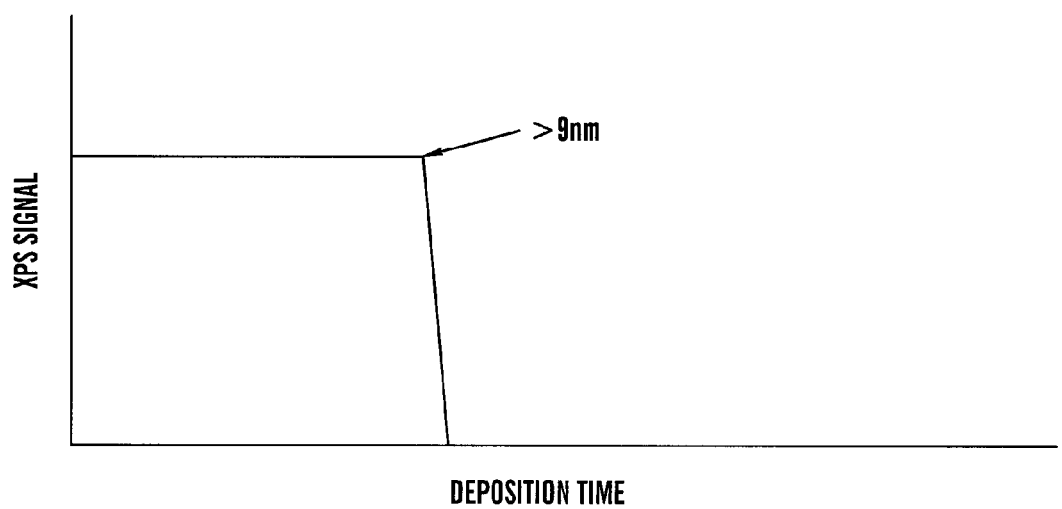
FIG. 3 illustrates endpoint detection in accordance with the invention.

FIG. 3 illustrates endpoint detection in accordance with the invention. While the previous paragraph describes the removal of a material, e.g. PC etch, FIG. 3 describes deposition of a material. FIG. 3 depicts the detectable photoelectron signal from a material in a set of layers undergoing patterning. In FIG. 3, a material is being deposited on the set of layers. With time, a decrease in the photoelectron signal occurs. More specifically, such decrease occurs when the layer undergoing thickness alteration is >9 nm thick, at which point in time the layer is too thick for the detection of the photoelectron emission.

Figure 4:
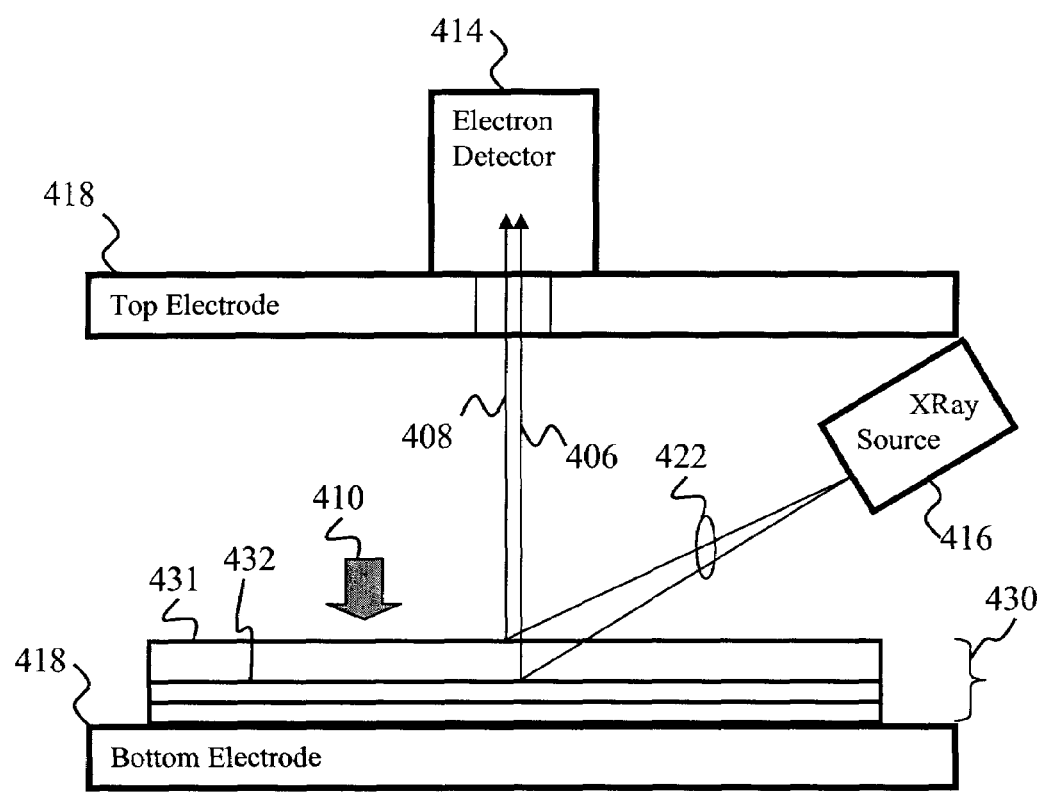
FIG. 4 illustrates an endpoint detection system in accordance with the invention.

FIG. 4 illustrates an endpoint detection system for either the removal or deposition of a material in accordance with the invention. As shown in FIG. 4, the invention detects endpoint in situ. As shown in FIG. 4, the semiconductor wafer rests within the alteration device 418 and the causation device 416 causes an emission of photoelectrons 408, while the semiconductor wafer undergoes patterning. The alteration device 418 includes, but is not limited to, a material removal or deposition tool. A material removal tool includes, but is not limited to, a plasma or RIE tool. The causation device 416 includes, but is not limited to, a standard x-ray photoelectron spectrometer. The detection device 414 is a photoelectron detector, such as but not limited to, a time of flight photoelectron detector.

A semiconductor wafer having a set of layers 430 may be placed inside a thickness alteration device 418. The set of layers 430 may include a topmost layer 431, a layer 432 underlying topmost layer 431 and other possible layers underneath thereof. In certain embodiments, topmost layer 431 may be referred to as a first layer and the underlying layer 432 may be referred to as a second layer. Topmost layer 431 may be a layer undergoing thickness alteration inside thickness alteration device 418. The alteration may be through etching or deposition (410), or any other techniques that are well known on the art.

An endpoint of thickness alteration may be detected in situ. While semiconductor wafer of set of layers 430 undergoes patterning, a causation device 416, which may be an X-ray source for example but is not limited to X-ray source, may cause emission 408 (first emission) of a plurality of photoelectrons from topmost layer 431 and emission 406 (second emission) of a plurality of photoelectrons from underlying layer 432. Emission 408 and 406 may be caused by irradiating the set of layers 430 through a plurality of photons 422 from causation device 416.

Emission 408 may have a signal unique to the material of topmost layer 431, and emission 406 may have a signal unique to the material of underlying layer 432. Emission 408 may be detected by an electron detector 414, and emission 406 may also be detected by electron detector 414 depending on a thickness of topmost layer 431. A thick topmost layer 431 may de-energize and thus cause photoelectrons from underlying layer 432 not to reach electron detector 414. Electron detector 414 may compare signals received and may determined an endpoint of thickness alteration upon detection of different signals. The different signals, which may be substantial, may be due to the diminishing or addition of emission of photoelectron from, for example, underlying layer 432.

While the invention has been particularly described in conjunction with a specific preferred embodiment and other alternative embodiments, it is evident that numerous alternatives, modifications and variations will be apparent to those skilled in the art in light of the foregoing description. It is therefore intended that the appended claims embrace all such alternatives, modifications and variations as falling within the true scope and spirit of the invention.

What is claimed is:

1. A method for detecting an endpoint during a thickness alteration of a first layer in a set of layers undergoing patterning in a thickness alteration device, said method comprising the steps of:
   placing said set of layers in said thickness alteration device;
   causing a first emission of a plurality of photoelectrons from said first layer undergoing thickness alteration in said set of layers;
   causing a second emission of a plurality of photoelectrons from a second layer in said set of layers, said second layer underlying said first layer undergoing thickness alteration;
   altering the thickness of said first layer in said set of layers; and,
   detecting in situ an endpoint of said thickness alteration upon receipt of said second emission while said first layer undergoes said thickness alteration.

2. A method as in claim 1, wherein said causing steps further comprise the step of irradiating said set of layers with a plurality of photons.

3. A method as in claim 1, wherein said first emission has a first signal unique to a material of said first layer undergoing thickness alteration and said second emission has a second signal unique to a material of said second layer underlying said first layer.

4. A method as in claim 3, wherein said detecting step further comprises the steps of:
   comparing said first and second signals; and,
   determining said endpoint when said first and second signals are substantially different.

5. A method as in claim 3, wherein said material of said first layer comprises at least one of an element and a compound and said set of layers comprises at least one of a semiconductor, a dielectric, and a conductor.

6. A method as in claim 3, wherein said material of said first layer undergoing thickness alteration and said material of said second layer underlying said first layer differ only in stoichiometry.

7. A method as in claim 1, wherein said endpoint detection occurs when said first layer undergoing thickness alteration is less than or equal to 9.0 nm thick.

8. A method for detecting an endpoint of a thickness alteration of a topmost layer in a set of layers undergoing patterning, said method comprising the steps of:
- placing said set of layers in a thickness alteration device;
- receiving an emission of a plurality of photoelectrons from a layer underlying said topmost layer in said set of layers; and,
- detecting in situ an endpoint of said thickness alteration of said topmost layer upon receipt of said emission or upon detection of diminishing of said emission while said topmost layer undergoes said thickness alteration inside said thickness alteration device.

9. A method as in claim 8 further comprising, the step of causing said emission of said plurality of photoelectrons.

10. A method as in claim 9, wherein said causing step further comprises the step of irradiating said set of layers with a plurality of photons.

11. A method as in claim 8, wherein said thickness alteration comprises one of depositing a material on said topmost layer and removing a material from said topmost layer.

12. A method as in claim 8, wherein said set of layers comprises at least one of a semiconductor, a dielectric, and a conductor.

13. A method as in claim 8, wherein said emission has a signal unique to a material of said layer underlying said topmost layer in said set of layers.

14. A method as in claim 13, wherein said material comprises at least one of an element and a compound.

15. A method as in claim 13, wherein material of said layers in said set differ only in stoichiometry.

16. A system for detection of an endpoint of a thickness alteration of a topmost layer in a set of layers undergoing patterning, said system comprising:
- an alteration device for altering the thickness of said topmost layer;
- a causation device for causing emission of a plurality of photoelectrons from one or more layers in said set of layers; and,
- a detection device for detecting an endpoint of said thickness alteration of said topmost layer upon receipt of said emission or upon detection of diminishing of said emission.

17. A system as in claim 16, wherein said alteration device comprises one of a removal tool and a deposition tool, said removal tool comprises one of a plasma tool and a RIE tool, said causation device comprises an x-ray photoelectron spectrometer, and said detection device comprises a time of flight photoelectron detector.

18. A method for detection of an endpoint of a thickness alteration of a topmost layer in a set of layers undergoing patterning in a thickness alteration device, said method comprising the steps of:
- causing a first emission of a plurality of photoelectrons from a first layer in said set of layers, said topmost layer undergoing thickness alteration, said first emission having a signal unique to a material comprising said first layer;
- causing a second emission of a plurality of photoelectrons from a second layer in said set of layers, said second emission having a signal unique to a material comprising said second layer;
- comparing said signals; and,
- detecting in situ an endpoint of said thickness alteration while said topmost layer undergoes said thickness alteration, when said signals are substantially different.

19. A method as in claim 18, wherein said topmost layer is said first layer and said signals are substantially different when said topmost layer is less than or equal to 9.0 nm thick.

* * * * *